March 21, 1967 R. L. BYRUM Plant Pat. 2,728
ROSE PLANT
Filed March 15, 1966
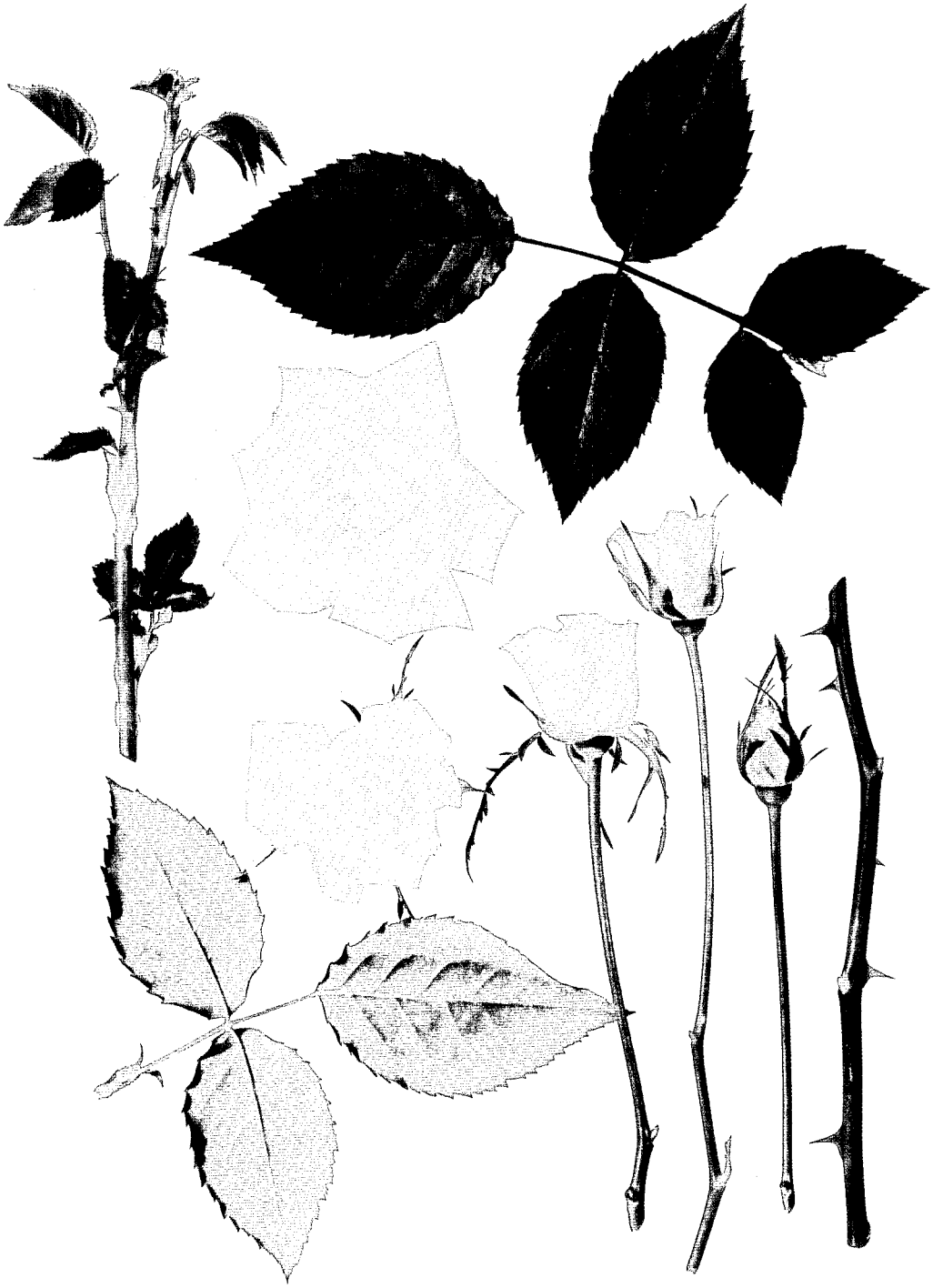
Inventor.
R. L. Byrum
By: Robb & Robb
Attorneys.

United States Patent Office

Plant Pat. 2,728
Patented Mar. 21, 1967

2,728
ROSE PLANT

Roy L. Byrum, Richmond, Ind., assignor to Joseph H. Hill Company, Richmond, Ind., a corporation of Indiana Filed Mar. 15, 1966, Ser. No. 534,540
1 Claim. (Cl. Plt.—22)

The present invention relates to a new and distinct variety of rose plant of the floribunda class, which was originated by me by crossing an unnamed and unpatented seedling of unidentified parentage, but identified in my breeding records as #58Q, with the variety known as "Rumba" (Plant Patent No. 1,919).

The primary objective of this breeding was to produce a new rose variety which combines the good flower production and orange flower color of the unnamed seed parent with the stronger stems, excellent foliage and good flower keeping qualities of the pollen parent, "Rumba." This objective was fully achieved, as evidenced by the following unique combination of characteristics which are outstanding in the new variety and which distinguish it from its parents, as well as from all other rose varieties of which I am aware:

(1) Abundant dark green glossy foliage which enhances and intensifies the flower color;

(2) Long and upright flower stems, with very few disbuds;

(3) Abundant production of flowers of bright orange general color tonality which is unusual in the class of greenhouse forcing rose varieties; and (4) Excellent keeping qualities of the flowers as cut flowers.

In comparison with its unnamed seed parent, which bears flowers of orange color and has very good growing habits except for weak flower stems, my new variety has retained these qualities with substantial improvement in the stems which are strong and straight.

As compared with its pollen parent, "Rumba," the new variety is better for greenhouse forcing, and produces larger blooms of more uniform color and on longer stems.

Asexual reproduction of my variety by grafting, as performed at Richmond, Ind., and also by budding, as performed at Livermore, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)), and Koster's Color Guide (hereinafter abbreviated as (K)), except where general color terms of ordinary dictionary significance are obvious:

Type: Bush; seedling; for greenhouse production of cut flowers.
Class: Floribunda.
Breeding: Seedling.
*Seed parent.*—An unnamed seedling of unidentified parentage.
*Pollen.*—"Rumba."
Propagation: Holds its distinguishing characteristics through succeeding propagations by both grafting and budding.

*Flower*

Locality where grown and observed: Richmond, Ind.
Flowers borne: Usually singly to stem, but sometimes in clusters; on stems of medium length.
Quantity of bloom: Abundant, in greenhouse.
Continuity: Continuous, in greenhouse.
Fragrance: Slight, in greenhouse. Nature—spicy.
Bud:
*Peduncle.*—Medium length; medium caliper; strong; erect. Bark—smooth; color—Boxwood Green, Plate 79 (K), with portions overlaid with Olive Brown, Plate 86 (K). Thorns—none. Prickles—none. Hairs—none.
*Before calyx breaks.*—Size—small. Form—short pointed; with a conspicuous neck; with foliaceous appendages on the surface of the bud; with slender foliaceous parts extending beyond the tip of the bud equal to ¼ or more of its length. Color—Scheele's Green, Plate 860 (W).
*As calyx breaks.*—Color (outside of petal)—Scheele's Green, Plate 860 (W).
*As first petal opens.*—Size—small. Form—short; pointed. Color: outside—Base Mimosa Yellow, Plate 602/1 (W), with upper portion Shrimp Red, Plate 616 (W); inside—Base Mimosa Yellow, Plate 602 (W), with upper portion Nasturtium Red, Plate 14/1 (W), and with a white vein extending from base ⅔ or more of its length.
*Opening.*—Opens up well in greenhouse, with no unusual characteristics observed.
Bloom:
*Size (when fully open).*—Small; from 2 inches to 2½ inches.
*Petalage.*—Very double; from 40 to 45 petals; arranged regularly.
*Form.*—Full and high-centered at first, but becoming flat; petals being at first very tightly rolled outward, but later becoming loosely rolled outward at maturity.
Petals:
*Texture.*—Moderately thick.
*Appearance.*—Inside—satiny. Outside—satiny.
*Shape.*—Outer petals—obovate, with apex retuse. Intermediate petals—obovate, with apex mucronate. Inner petals—obovate, with apex mucronate.

This description of a newly opened flower was made from a rose grown in a greenhouse during the month of November at Richmond, Ind.:

*Color.*—Outer petals: outside surface—lower portion Aureolin, Plate 3/1 (W), changing to Shrimp Red, Plate 616/2 (W) at top; inside surface—lower portion Aureolin, Plate 3 (W), changing to petals: Poppy Red, Plate 16/1 (W) at top. Intermediate outside surface—lower portion Aureolin, Plate 3/1 (W), changing to Nasturtium Orange, Plate 610/2 (W) at top; inside surface—lower portion Aureolin, Plate 3 (W), changing to Nasturtium Red, Plate 14/1 (W) at top. Inner petals: outside surface—lower portion Aureolin, Plate 3/1 (W), changing to Nasturtium Orange, Plate 610/1 (W) at top; inside surface—lower portion Aureolin, Plate 3 (W), changing to Nasturtium Red, Plate 14/1 (W) at top.

This description was made from a rose that was open for three days in a greenhouse during the month of November at Richmond, Ind.:

*Color.*—Outer petals: outside surface—lower portion Aureolin, Plate 3/2 (W), changing to French Rose, Plate 520/1 (W) at top; inside surface—lower portion Aureolin, Plate 3/1 (W), changing to Empire Rose, Plate 0621/1 (W) at top. Intermediate petals: outside surface—lower portion Aureolin, Plate 3/2 (W), changing to French Rose, Plate 520/3 (W) at top; inside surface—lower portion Aureolin, Plate 3/1 (W), changing through Marigold Orange, Plate 11/2 (W) to Empire Rose, Plate 0621/1 (W) at top. Inner petals: outside surface—lower portion Aureolin, Plate 3/2 (W), changing to French Rose, Plate 520/3 (W) at top; inside surface—lower portion Aureolin, Plate 3/1 (W), changing to Shrimp Red, Plate 616/1 (W) at top.

*General color effect.*—Newly opened flower—Marigold Orange, Plate 11/2 (W). Three days open—Shrimp Red, Plate 616/1 (W).

*Behavior of petals.*—Persist in greenhouse.

*Flower longevity.*—Cut roses grown in greenhouse and kept at livingroom temperatures—from 5 to 7 days in November.

*Reproductive organs*

Stamens: Medium number; arranged regularly about pistils.

Filaments: Medium length; most with anthers. Color—Chinese Yellow, Plate 606/1 (W).

Anthers: Small; all open at once. Color—Yellow Ochre, Plate 07/1 (W).

Pollen: Abundant. Color—Orange Buff, Plate 507/1 (W).

Pistils: Medium number.

Styles: Even; medium length; moderately thin; bunched. Color—Cherry, Plate 722/3 (W).

Stigma: Color—Empire Yellow, Plate 603/3 (W).

Hips: None.

Sepals: Permanent; medium length; spear-shaped. Color: inside—Scheele's Green, Plate 860/2 (W), overlaid with white fuzz; outside—Scheele's Green, Plate 860/1 (W).

Seeds: None.

*Plant*

Foliage:

*Leaves.*—Compound of 3, 5 and 7 leaflets; abundant; medium size; heavy; glossy.

*Leaflets.* — Shape — ovoid. Apex—acuminate. Base—round. Margin—simply serrate.

*Color.* — Mature: upper surface — near Spinach Green, Plate 0960 (W); under surface—near Spinach Green, Plate 0960/3 (W). Young: upper surface—Fern Green, Plate 0862/1 (W), overlaid with Oxblood Red, Plate 00823/1 (W); under surface—Fern Green, Plate 0862/3 (W), overlaid with Oxblood Red, Plate 00823/3 (W).

*Rachis (the supporting stem of the compound leaf).*—Medium heavy. Upper side—grooved. Under side—prickly.

*Stipules.*—Medium length; medium width; with short points turning out at an angle of less than 45°.

Growth:

*Habit.*—Bush; upright; much-branched.

*Growth.*—Vigorous.

*Canes.*—Medium diameter.

*Main stems.*—Color—Spinach Green, Plate 0960/2 (W), with streaks of Van Dyck Brown, Plate 96 (K). Thorns—several; straight; with short, narrow base; color—Van Dyck Brown, Plate 96 (K). Prickles—none. Hairs—none.

*Branches.*—Color—Spinach Green, Plate 0960/1 (W), with some areas lightly shaded with Maroon, Plate 1030/2 (W). Thorns—several; medium length; straight; with short, narrow base; color—Chrysanthemum Crimson, Plate 824/3 (W). Prickles—none. Hairs—none.

*New shoots.*—Color—Oxblood Red, Plate 00823 (W). Thorns—few; medium length; hooked downward; with long, narrow base; color—Chrysanthemum Crimson, Plate 824/3 (W). Prickles—none. Hairs—none.

I claim:

A new and distinct variety of rose plant of the floribunda class, substantially as herein shown and described, characterized particularly as to novelty by the unique combination of abundant dark green glossy foliage which enhances and intensifies the flower color; long and upright flower stems, with very few disbuds; abundant production of flowers of bright orange general color tonality which is unusual in the class of greenhouse forcing rose varieties; and excellent keeping qualities of the flowers as cut flowers.

No references cited.

ABRAHAM G. STONE, *Primary Examiner.*

ROBERT E. BAGWILL, *Assistant Examiner.*